United States Patent
Annangi et al.

(10) Patent No.: US 11,803,967 B2
(45) Date of Patent: Oct. 31, 2023

(54) METHODS AND SYSTEMS FOR BICUSPID VALVE DETECTION WITH GENERATIVE MODELING

(71) Applicant: GE Precision Healthcare LLC, Milwaukee, WI (US)

(72) Inventors: Pavan Annangi, Bangalore (IN); Rahul Venkataramani, Bangalore (IN); Deepa Anand, Bangalore (IN); Eigil Samset, Oppegård (NO)

(73) Assignee: GE Precision Healthcare LLC, Milwaukee, WI (US)

( * ) Notice: Subject to any disclaimer, the term of this patent is extended or adjusted under 35 U.S.C. 154(b) by 338 days.

(21) Appl. No.: 17/220,770

(22) Filed: Apr. 1, 2021

(65) Prior Publication Data

US 2022/0319006 A1 Oct. 6, 2022

(51) Int. Cl.
*G06T 7/00* (2017.01)
*A61B 8/08* (2006.01)
(Continued)

(52) U.S. Cl.
CPC .......... *G06T 7/0014* (2013.01); *A61B 8/0883* (2013.01); *A61B 8/5223* (2013.01); *G06F 18/2148* (2023.01); *G06F 18/24* (2023.01); *G06N 3/045* (2023.01); *G06N 3/088* (2013.01); *G06V 10/25* (2022.01); *G06V 10/98* (2022.01);
(Continued)

(58) Field of Classification Search
CPC ......... G06T 7/0014; G06T 2207/10016; G06T 2207/10132; G06T 2207/20081; G06T 2207/30048; G06T 2207/20084; G06T 7/0012; A61B 8/0883; A61B 8/5223; A61B 8/486; A61B 8/488; A61B 8/0891; A61B 8/5215; G06F 18/2148; G06F 18/24; G06N 3/045; G06N 3/088; G06N 3/047;
(Continued)

(56) References Cited

U.S. PATENT DOCUMENTS 9,700,219 B2 7/2017 Sharma et al.
2013/0040838 A1\* 2/2013 Huggins .............. C12Q 1/6883
536/24.31

(Continued)

OTHER PUBLICATIONS

Isner, J., et al., "Catheter-Based Intravascular Ultrasound Discriminates Bicuspid From Tricuspid Valves in Adults With Calcific Aortic Stenosis", J Am Coll Cardiol vol. 15, No. 6, May 1990:1310-1317.\*

(Continued)

*Primary Examiner* — Xuemei G Chen
(74) *Attorney, Agent, or Firm* — McCoy Russell LLP (57) ABSTRACT

Various methods and systems are provided for bicuspid valve detection with ultrasound imaging. In one embodiment, a method comprises acquiring ultrasound video of a heart over at least one cardiac cycle, identifying frames in the ultrasound video corresponding to at least one cardiac phase, and classifying a cardiac structure in the identified frames as a bicuspid valve or a tricuspid valve. A generative model such as a variational autoencoder trained on ultrasound image frames at the at least one cardiac phase may be used to classify the cardiac structure. In this way, relatively rare occurrences of bicuspid aortic valves may be automatically detected during regular cardiac ultrasound screenings.

19 Claims, 8 Drawing Sheets

(51) Int. Cl.
G06N 3/088 (2023.01)
G06V 10/25 (2022.01)
G06V 10/98 (2022.01)
G06F 18/24 (2023.01)
G06F 18/214 (2023.01)
G06N 3/045 (2023.01)

(52) U.S. Cl.
CPC ............ *G06T 2207/10016* (2013.01); *G06T 2207/10132* (2013.01); *G06T 2207/20081* (2013.01); *G06T 2207/30048* (2013.01); *G06V 2201/031* (2022.01)

(58) Field of Classification Search
CPC .. G06V 10/25; G06V 10/98; G06V 2201/031; G06V 10/764; G06V 10/82
See application file for complete search history.

(56) References Cited

U.S. PATENT DOCUMENTS

| | | | | |
|---|---|---|---|---|
| 2015/0272546 | A1* | 10/2015 | Cheon | G16H 50/30 600/440 |
| 2015/0327838 | A1* | 11/2015 | Francis | A61B 8/4433 600/459 |
| 2017/0014105 | A1* | 1/2017 | Chono | A61B 8/14 |
| 2019/0008480 | A1* | 1/2019 | Gerard | A61B 8/5246 |
| 2019/0099162 | A1* | 4/2019 | Keshet | G06T 7/0016 |
| 2019/0304095 | A1* | 10/2019 | Veni | G06T 7/174 |
| 2021/0150693 | A1* | 5/2021 | Fornwalt | G16H 50/30 |
| 2021/0196228 | A1* | 7/2021 | Raju | A61B 8/466 |
| 2021/0209757 | A1* | 7/2021 | Min | A61B 5/7475 |
| 2021/0259664 | A1* | 8/2021 | Hare, II | A61B 8/463 |
| 2021/0275135 | A1* | 9/2021 | Choi | A61B 8/4488 |
| 2022/0044815 | A1* | 2/2022 | Shaw | G16H 50/30 |
| 2022/0061809 | A1* | 3/2022 | Veronesi | A61B 8/466 |
| 2022/0273261 | A1* | 9/2022 | Steen | G06N 3/02 |

OTHER PUBLICATIONS

Alkadhi, H., et al., "Cardiac CT for the Differentiation of Bicuspid and Tricuspid Aortic Valves: Comparison With Echocardiography and Surgery", AJR:195, pp. 900-908, Oct. 2010.*

Wojnarski, C.M., et al., "Machine-learning phenotypic classification of bicuspid aortopathy", The Journal of Thoracic and Cardiovascular Surgery, vol. 155, No. 2, 2017.*

Fries, Jason A., et al. "Weakly supervised classification of aortic valve malformations using unlabeled cardiac MRI sequences." Nature communications 10.1 (2019): 3111.*

Wessler, B. et al., "Identification of Severe Aortic Stenosis Using Deep Learning," Journal of the American College of Cardiology, vol. 75, No. 11, Mar. 2020, 1 page.

Kwon, J. et al., "Deep Learning-Based Algorithm for Detecting Aortic Stenosis Using Electrocardiology," Journal of the American Heart Association, vol. 9, No. 7, Apr. 9, 2020, 16 pages.

* cited by examiner

METHODS AND SYSTEMS FOR BICUSPID VALVE DETECTION WITH GENERATIVE MODELING

FIELD

Embodiments of the subject matter disclosed herein relate to ultrasound imaging, and more specifically to detecting bicuspid aortic valves with ultrasound imaging.

BACKGROUND

Aortic valve stenosis or aortic stenosis occurs when the aortic valve of a heart narrows, thereby resulting in an increased blood flow pressure gradient at the aortic valve opening. The aortic valve does not fully open and so blood flow from the heart to the aorta is reduced. The possibility of aortic stenosis is significantly elevated if the aortic valve is bicuspid rather than tricuspid, where the aortic valve includes only two leaflets rather than the typical three leaflets. Such bicuspid aortic valves are relatively rare and occur in less than two percent of the normal population.

Ultrasound is the primary imaging modality used to screen for aortic stenosis. Early detection of a bicuspid aortic valve may enable proactive intervention and treatment to potentially reduce the likelihood of aortic stenosis. However, the presence of a bicuspid aortic valve is difficult to detect during regular screening procedures due to the low occurrence and the difficulty in visually distinguishing bicuspid leaflets from tricuspid leaflets.

BRIEF DESCRIPTION

In one embodiment, a method comprises acquiring ultrasound video of a heart over at least one cardiac cycle, identifying frames in the ultrasound video corresponding to at least one cardiac phase, and classifying a cardiac structure in the identified frames as a bicuspid valve or a tricuspid valve. A generative model such as a variational autoencoder trained on ultrasound image frames at the at least one cardiac phase may be used to classify the cardiac structure. In this way, relatively rare occurrences of bicuspid aortic valves may be automatically detected during regular cardiac ultrasound screenings.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 1:
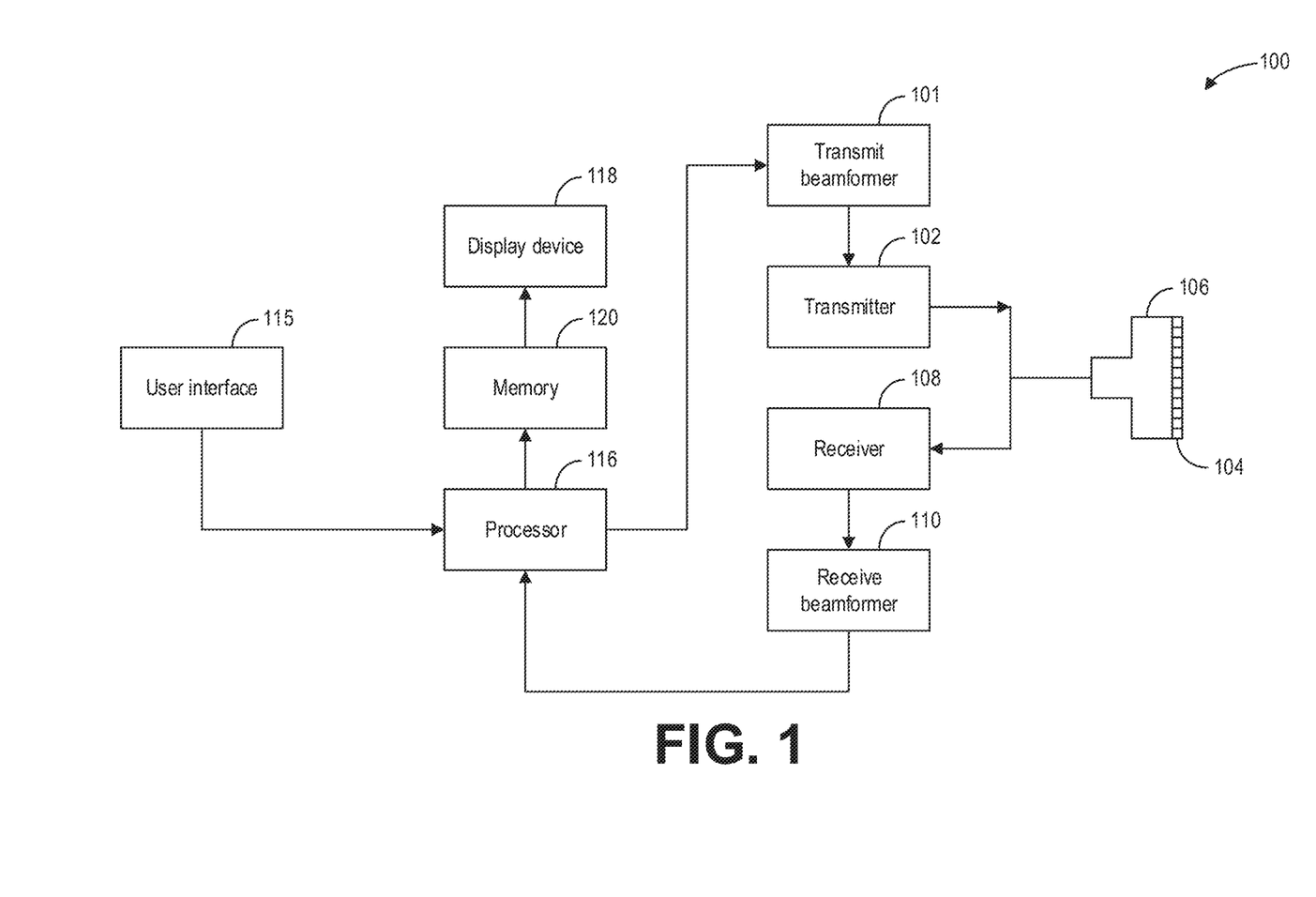
FIG. 1 shows a block diagram illustrating an example ultrasound imaging system, according to an embodiment.
Figure 3:
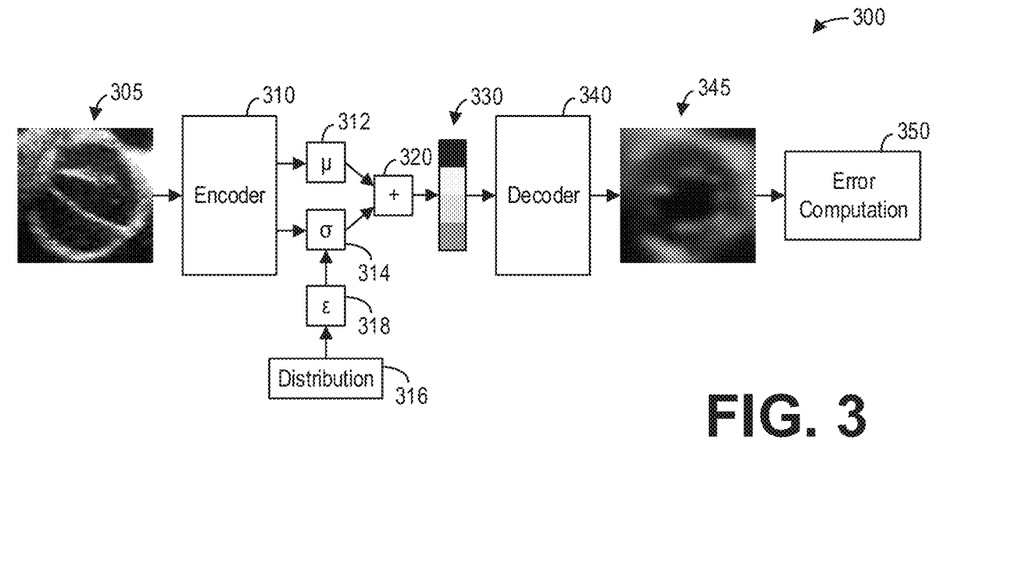
FIG. 3 shows a block diagram illustrating an example architecture for a generative model configured to classify an anatomical structure in an ultrasound image frame, according to an embodiment.
Figure 4:
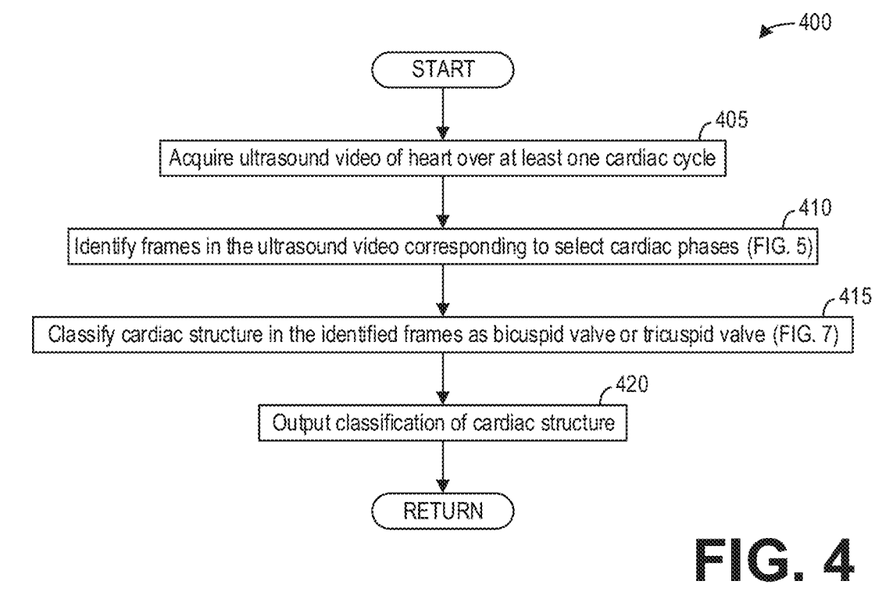
FIG. 4 shows a high-level flow chart illustrating an example method for classifying an anatomical structure in ultrasound video, according to an embodiment.
Figure 5:
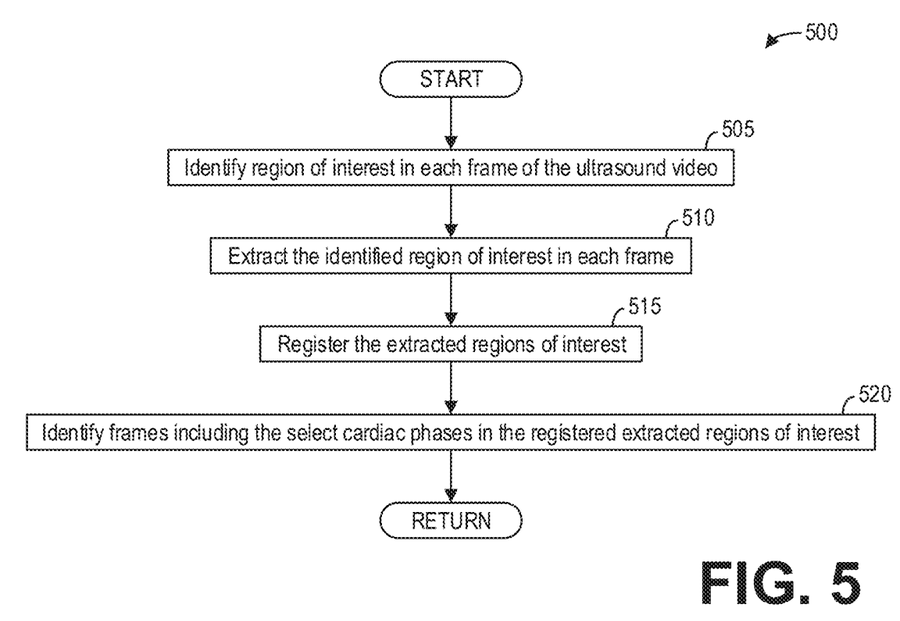
FIG. 5 shows a high-level flow chart illustrating an example method for identifying key frames in an ultrasound video including an anatomical structure at a given cardiac phase, according to an embodiment.
Figure 6:
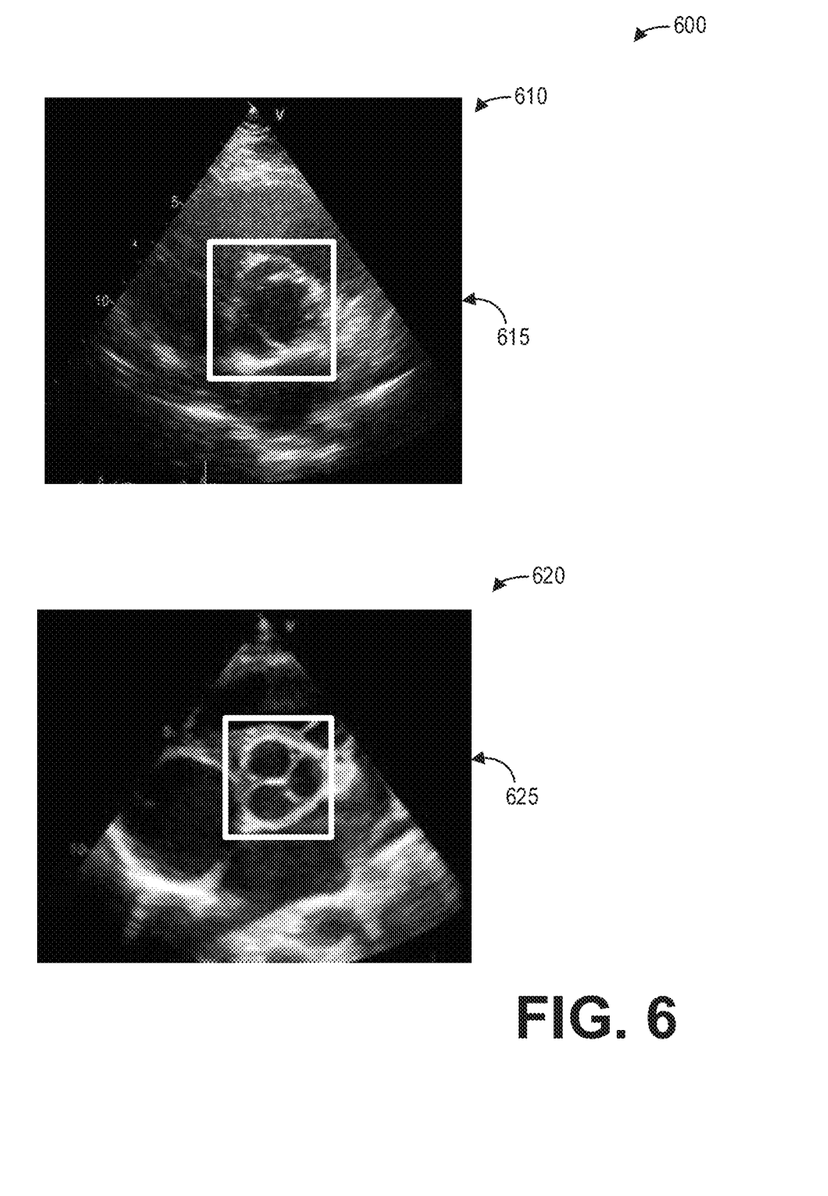
FIG. 6 shows a set of example ultrasound images illustrating an example identification of key frames including an anatomical structure at a given cardiac phase, according to an embodiment.
Figure 7:
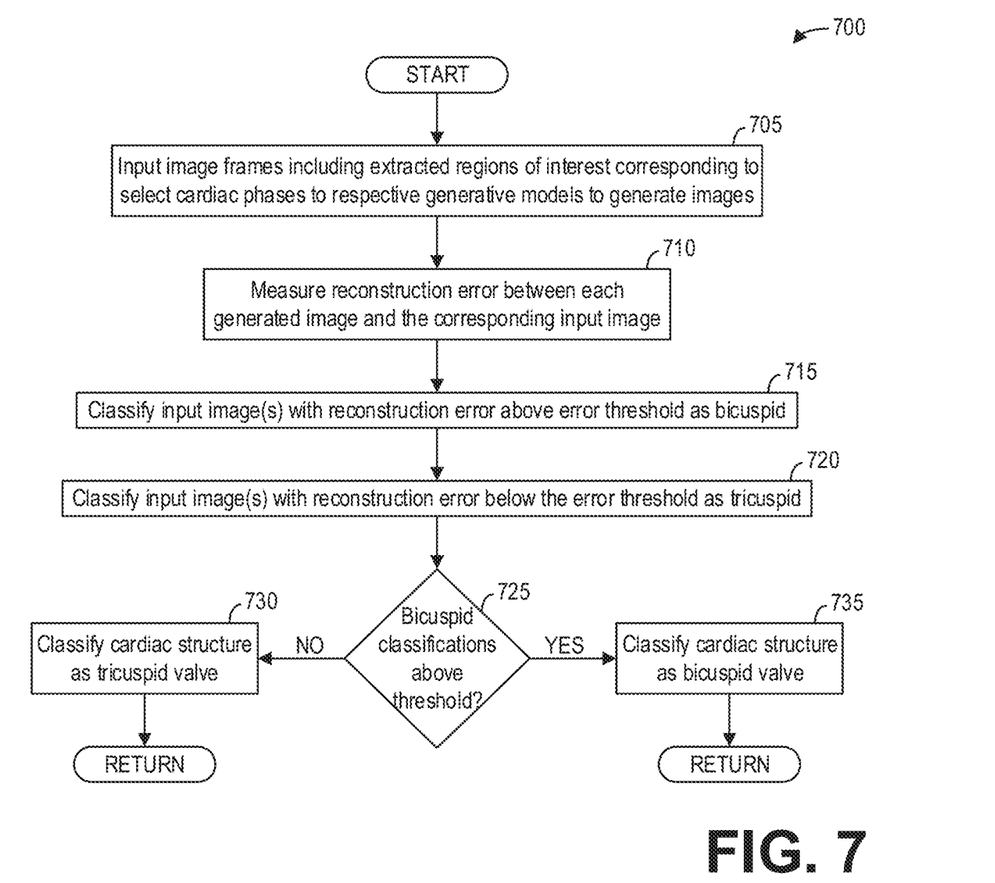
FIG. 7 shows a high-level flow chart illustrating an example method for classifying an anatomical structure as a bicuspid or tricuspid valve, according to an embodiment.
Figure 8:
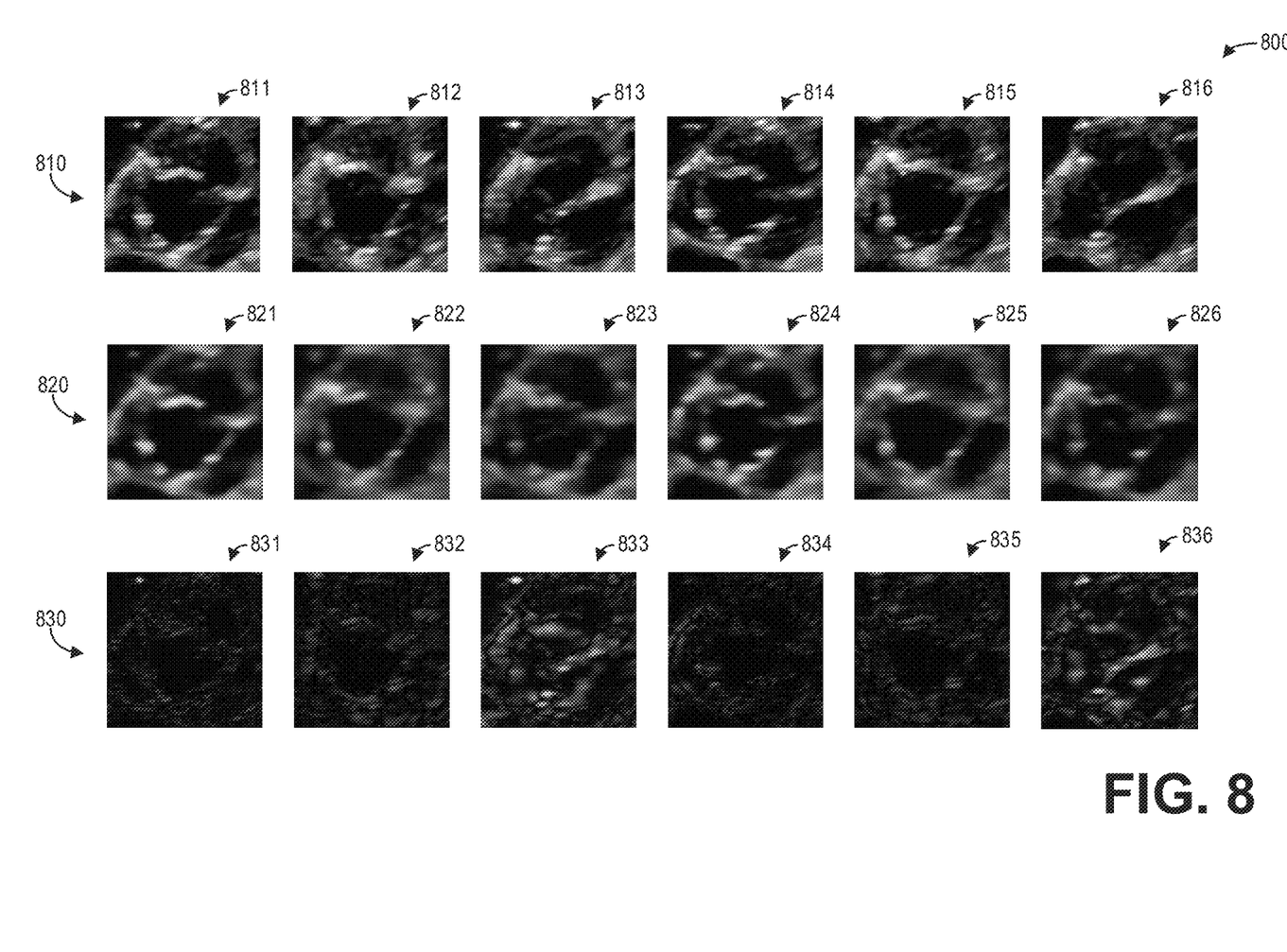
FIG. 8 shows a set of images illustrating generated images and reconstruction errors for key frames in an ultrasound video resulting in classification of a tricuspid valve, according to an embodiment.
Figure 9:
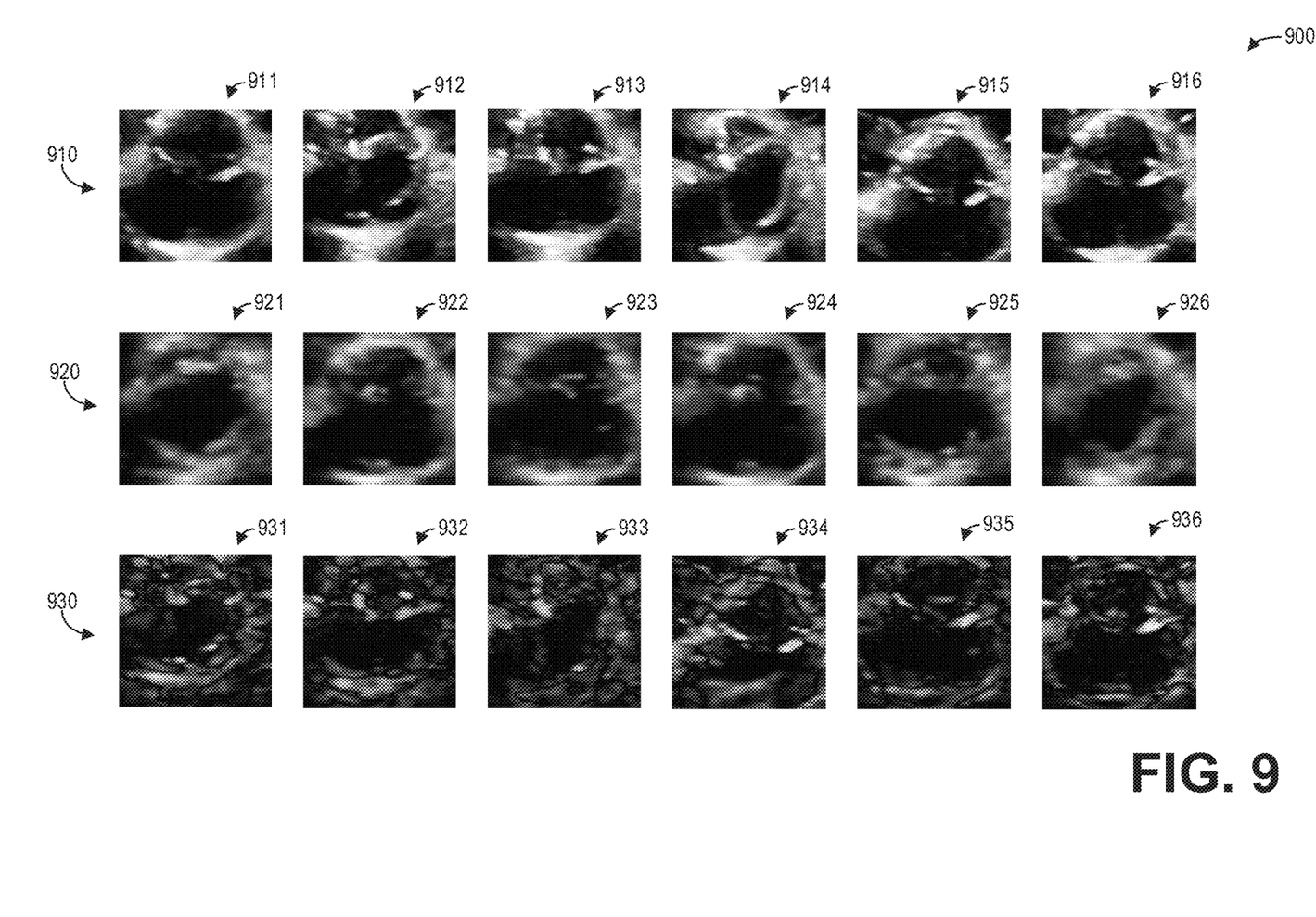
FIG. 9 shows a set of images illustrating generated images and reconstruction errors for key frames in an ultrasound video resulting in classification of a bicuspid valve, according to an embodiment.

The following description relates to various embodiments of ultrasound imaging. In particular, methods and systems for automatic detection of bicuspid valves with an ultrasound imaging system are provided. An example of an ultrasound imaging system that may be used to acquire images in accordance with the present techniques is shown in FIG. 1. The ultrasound imaging system may be communicatively coupled to an image processing system, such as the image processing system of FIG. 2. The image processing system may include one or more deep learning models, such as one or more neural networks and one or more generative models, stored in non-transitory memory. A generative model configured as a variational autoencoder, as shown in FIG. 3, may be trained on ultrasound images of tricuspid valves at a select cardiac phase. Ultrasound video comprising a sequence of ultrasound image frames or ultrasound images may then be processed, for example as shown in FIG. 4, with such a trained generative model to classify a cardiac structure in the ultrasound video as a bicuspid valve or a tricuspid valve. The cardiac structure in the ultrasound video may be extracted from the ultrasound video, as shown in FIGS. 5 and 6, and frames corresponding to select cardiac phases may then be identified. A method for classifying the cardiac structure using generative models, as shown in FIG. 7, may then include using the extracted ultrasound images of the cardiac structure at the select cardiac phases as inputs to respective generative models. Since the generative models are trained on images of tricuspid valves, images output by the generative models may have a relatively high reconstruction error if the input image depicts a bicuspid valve. By processing a plurality of ultrasound images acquired over multiple cardiac cycles and obtaining a plurality of classifications of the cardiac structure as bicuspid or tricuspid, the individual classifications may be aggregated to determine a final classification of the cardiac structure as bicuspid or tricuspid, as shown in FIGS. 8 and 9. Thus, automatic detection of a bicuspid valve may be obtained using deep learning models despite the data imbalance problem wherein less training data for bicuspid valves are available compared to tricuspid valves, which would otherwise cause significant issues for training a deep learning model to classify a cardiac structure as a bicuspid valve.

Turning now to the figures, FIG. 1 shows a schematic diagram of an ultrasound imaging system 100 in accordance with an embodiment of the disclosure. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic spherical wave. In this way, transducer elements 104 may convert electronic transmit signals into acoustic transmit beams.

After the elements 104 of the probe 106 emit pulsed ultrasonic signals into a body (of a patient), the pulsed ultrasonic signals are back-scattered from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data. Additionally, transducer element 104 may produce one or more ultrasonic pulses to form one or more transmit beams in accordance with the received echoes.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms "scan" or "scanning" may also be used in this disclosure to refer to acquiring data through the process of transmitting and receiving ultrasonic signals. The term "data" may be used in this disclosure to refer to either one or more datasets acquired with an ultrasound imaging system. In one embodiment, data acquired via ultrasound system 100 may be used to train a machine learning model. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term "electronic communication" may be defined to include both wired and wireless communications. The processor 116 may control the probe 106 to acquire data according to instructions stored on a memory of the processor 116, and/or memory 120. The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the RF data and generates raw data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates that are considerably faster than 20 frames/sec while other embodiments may have real-time frame-rates slower than 7 frames/sec. The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate of, for example, 10 Hz to 30 Hz (e.g., 10 to 30 frames per second). Images generated from the data may be refreshed at a similar frame-rate on display device 118. Other embodiments may acquire and display data at different rates. For example, some embodiments may acquire data at a frame-rate of less than 10 Hz or greater than 30 Hz depending on the size of the frame and the intended application. A memory 120 is included for storing processed frames of acquired data. In an exemplary embodiment, the memory 120 is of sufficient capacity to store at least several seconds' worth of frames of ultrasound data. The frames of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines and/or frames are stored in memory and may include timing information indicating a time at which the image lines and/or frames were stored in memory. The modules may include, for example, a scan conversion module to perform scan conversion operations to convert the acquired images from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional ultrasound scan, a block of data comprising scan lines and their samples is generated. After back-end filters are applied, a process known as scan conversion is performed to transform the two-dimensional data block into a displayable bitmap image with additional scan information such as depths, angles of each scan line, and so on. During scan conversion, an interpolation technique is applied to fill missing holes (i.e., pixels) in the resulting image. These missing pixels occur because each element of the two-dimensional block should typically cover many pixels in the resulting image. For example, in current ultrasound imaging systems, a bicubic interpolation is applied which leverages neighboring elements of the two-dimensional block. As a result, if the two-dimensional block is relatively small in comparison to the size of the bitmap image, the scan-converted image will include areas of poor or low resolution, especially for areas of greater depth.

Figure 2:
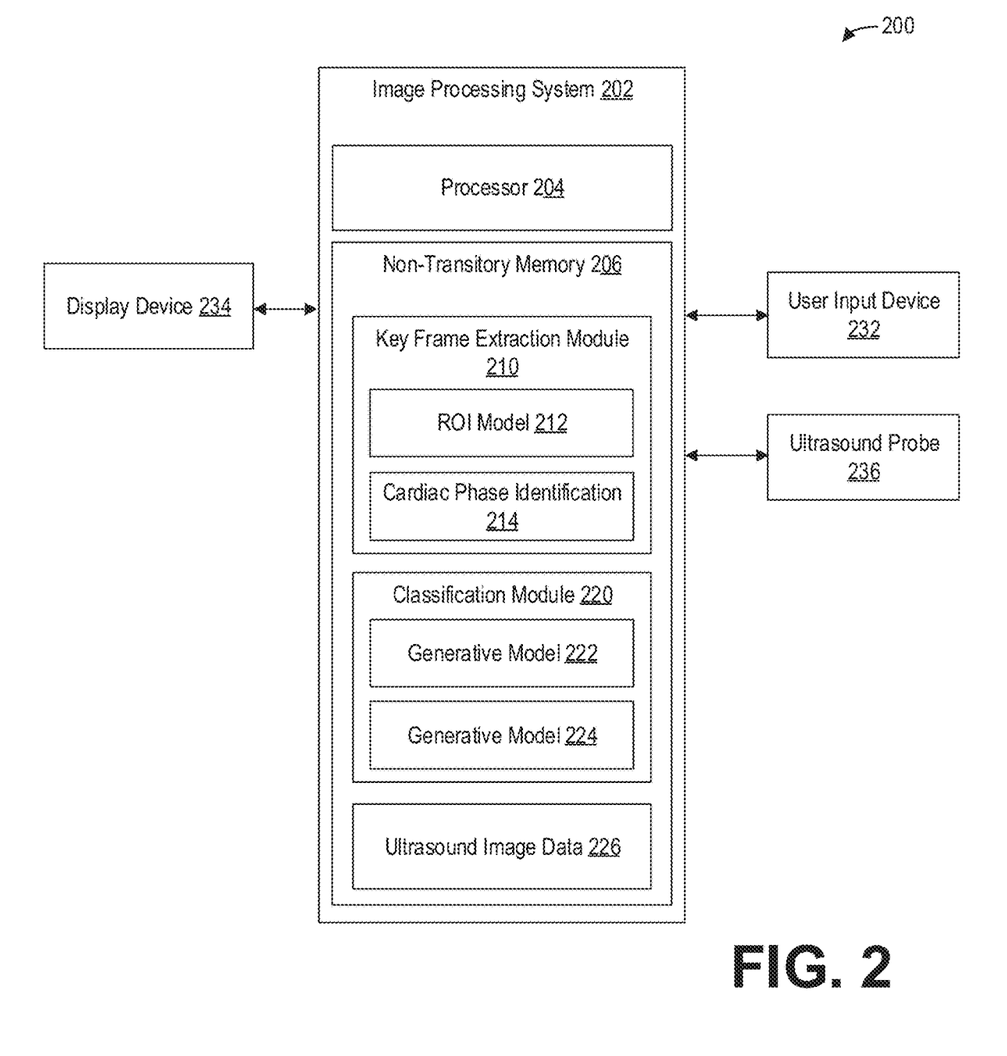
FIG. 2 shows a block diagram illustrating an example image processing system configured to classify an anatomical structure in ultrasound image frames using generative models, according to an embodiment.

FIG. 2 shows a block diagram illustrating an example system 200 including an image processing system 202 configured to classify an anatomical structure in ultrasound image frames, according to an embodiment. In some embodiments, the image processing system 202 may be provided in the ultrasound imaging system 100 as the processor 116 and memory 120. In some embodiments, at least a portion of image processing system 202 is disposed at a device (e.g., edge device, server, and so on) communicatively coupled to the ultrasound imaging system 100 via wired and/or wireless connections. In some embodiments, at least a portion of the image processing system 202 is disposed at a separate device (e.g., a workstation) which can receive images from the ultrasound imaging system 100 or from a storage device (not shown) which stores the image data generated by the ultrasound imaging system 100. The image processing system 202 may be communicatively coupled to a user input device 232 and a display device 234. The user input device 232 may comprise the user interface 115 of the ultrasound imaging system 100, while the display device 234 may comprise the display device 118 of the ultrasound imaging system 100, in some examples. The image processing system 202 may further be communicatively coupled to an ultrasound probe 236, which may comprise the ultrasound probe 106 described hereinabove, for example.

The image processing system 202 includes a processor 204 configured to execute machine readable instructions stored in non-transitory memory 206 of the image processing system 202. The processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store a key frame extraction module 210, a classification module 220, and ultrasound image data 226. The key frame extraction module 210 is configured to extract key frames including a region of interest (ROI) from ultrasound image data 226. The key frame extraction module 210 may thus comprise a region of interest (ROI) model module 212 and a cardiac phase identification module 214. The ROI model module 212 may comprise a deep learning model (e.g., a deep learning neural network) and instructions for implementing the deep learning model to identify a desired ROI within an ultrasound image. The ROI model module 212 may include trained and/or untrained neural networks and may further include various data or metadata pertaining to the one or more neural networks stored therein. As an illustrative and non-limiting example, the deep learning model of the ROI model module 212 may comprise a region-based convolutional neural network (R-CNN) such as mask R-CNN. The target ROI may comprise the aortic valve region in a heart, and so the ROI model module 212 may extract an ROI corresponding to the aortic valve region in an ultrasound image of a heart. The ROI model module 212 further temporally aligns ROIs in a sequence of ultrasound images (e.g., throughout an ultrasound video comprising a sequence of ultrasound images) in order to remove motion from the probe 236 or the patient being imaged beyond motion within the ROI.

The cardiac phase identification module 214 is configured to identify key cardiac phases in the extracted ROIs from the ROI model module 212. For example, the cardiac phase identification module 214 processes each extracted ROI from the ROI model module 212 and selects the frames that correspond to key cardiac phases. The key cardiac phases may comprise, for example, one or more of end-diastole (ED), end-systole (ES), diastole, and systole. To that end, the cardiac phase identification module 214 may process the extracted ROIs by modeling the sequence of extracted ROI frames as a linear combination of ED and ES frames, and applying non-negative matrix factorization (NMF) to identify the key frames. The key frame extraction module 210 thus takes ultrasound video (i.e., an ordered sequence of ultrasound image frames) as an input, and outputs key frames comprising extracted ROIs at key cardiac phases.

The classification module 220 comprises at least two generative models configured to generatively model the ROI during the key cardiac phases. For example, a first generative model 222 is configured to generatively model a first cardiac phase, while a second generative model 224 is configured to generatively model a second cardiac phase. As an illustrative and non-limiting example, the first generative model 222 may be trained to generatively model the aortic valve during the end-systolic phase, while the second generative model 222 may be trained to generatively model the aortic valve during the end-diastolic phase. In some examples, the classification module 220 may include more than two generative models, wherein each generative model is trained for a corresponding cardiac phase, while in other examples, the classification module 220 may include a single generative model trained on a single cardiac phase. The generative models 222 and 224 may comprise variational autoencoders (VAEs), generative adversarial networks (GANs), or another type of deep generative model. As an illustrative example, the generative models 222 and 224 may comprise VAEs configured to generatively model a tricuspid aortic valve during the end-systolic phase and the end-diastolic phase, respectively. An example generative model is described further herein with regard to FIG. 3.

FIG. 3 shows a block diagram illustrating an example architecture for a generative model 300 configured to classify an anatomical structure in an ultrasound image frame, according to an embodiment. In particular, the generative model 300 comprises a variational autoencoder configured to process an input ultrasound image 305 and outputs a generated image 345. To that end, the generative model 300 comprises an encoder 310 configured to encode the input ultrasound image 305 into a low-dimensional representation 330, and a decoder 340 configured to decode the low-dimensional representation 330 into the generated image 345.

The encoder 310 comprises a neural network configured to accept the input ultrasound image 305 as an input and output a representation of the input ultrasound image 305 in latent space. The encoder 310 thus comprises at least two layers comprising a plurality of neurons or nodes, wherein the last layer in the encoder 310 comprises a fewest number of neurons such that the encoder 310 decreases the dimensionality of the input ultrasound image 305 into latent space corresponding to the last layer of the encoder 310. Instead of outputting the latent variables of the last layer of the encoder 310, the encoder 310 outputs a mean (μ) tensor 312 and a standard deviation or variance (σ) tensor 314 comprising the mean values and standard deviations, respectively, of the encoded latent distributions.

In order to randomize the latent values from the input ultrasound image 305 encoded as the mean tensor 312 and the variance tensor 314, the generative model 300 randomly samples a distribution 316, which may comprise a unit Gaussian distribution as an illustrative example, to form a randomly-sampled distribution tensor 318. The variance tensor 314 is multiplied with the randomly-sampled distribution tensor 318 and then summed 320 with the mean tensor 312 to form the low-dimensional representation 330 of the input ultrasound image 305. This reparameterization through the distribution tensor 318 enables error backpropagation and thus training of the encoder 310.

The low-dimensional representation 330 of the input ultrasound image 305 is then input to the decoder 340 which decodes the low-dimensional representation 330 into the generated image 345. The decoder 340 comprises a neural network configured to accept the low-dimensional representation 330 as input and output the generated image 345. The decoder 340 thus comprises at least one layer comprising a plurality of neurons or nodes.

During training of the generative model 300, a loss function comprising a reconstruction error and a Kulback-Leibler (KL) divergence error are minimized. Minimizing the reconstruction error, which comprises a difference between the input ultrasound image 305 and the generated image 345, improves the overall performance of the encoder-decoder architecture. The reconstruction error is computed at the error computation 350 of the generative model 300. Minimizing the KL divergence error in latent space regularizes the distributions output by the encoder 310, namely the mean tensor 312 and the variance tensor 314, such that the tensors 312 and 314 are close to a standard normal distribution such as the unit Gaussian distribution 316. As one example, backpropagation and gradient descent with the loss function may be used to update the weights and biases of the encoder 310 and the decoder 340 during training of the generative model 300.

Due to the rarity of bicuspid valves relative to tricuspid valves, the generative model 300 is trained on input ultrasound images of tricuspid valves. In this way, when the input ultrasound image 305 comprises an image of a tricuspid valve, the trained generative model 300 outputs a generated image 345 of a tricuspid valve with minimal reconstruction error, or a minimal difference between the input ultrasound image 305 and the generated image 345. In contrast, when the input ultrasound image 305 comprises an image of a bicuspid valve, the trained generative model 300 outputs a generated image 345 that depicts an anatomical structure closer to a tricuspid valve than a bicuspid valve. Consequently, the reconstruction error between the input ultrasound image 305 and the generated image 345 may be relatively high and above an error threshold because the generative model 300 is trained on images of tricuspid valves instead of bicuspid valves. As discussed further herein, bicuspid valves may be detected by consistently measuring reconstruction errors above such an error threshold with the trained generative model 300. The error computation 350 may thus measure the reconstruction error and compare the measured reconstruction error to an error threshold. Further, the generative model 300 may be trained on ultrasound images of a tricuspid valve at a key cardiac phase, such as the end-diastolic phase or the end-systolic phase. As discussed hereinabove, the generative model 300 may be implemented as the first generative model 222 and the second generative model 224, wherein the first generative model 222 is trained on ultrasound images of tricuspid valves at an end-diastolic phase while a the second generative model 224 is trained on ultrasound images of tricuspid valves at an end-systolic phase.

FIG. 4 shows a high-level flow chart illustrating an example method 400 for classifying an anatomical structure in ultrasound video, according to an embodiment. In particular, method 400 relates to analyzing ultrasound video to classify a cardiac structure depicted in the ultrasound video as a bicuspid valve or a tricuspid valve. Method 400 is described with regard to the system and components of FIGS. 1-3, though it should be appreciated that the method 400 may be implemented with other systems and components without departing from the scope of the present disclosure. Method 400 may be implemented as executable instructions in non-transitory memory, such as the non-transitory memory 206, that when executed by a processor, such as the processor 204, cause the processor to perform the actions described herein below.

Method 400 begins at 405. At 405, method 400 acquires ultrasound video of a heart over at least one cardiac cycle. The ultrasound video may comprise a sequence of ultrasound image frames of a heart acquired over a plurality of cardiac cycles. The ultrasound image frames of the ultrasound video may comprise short axis images across the one or more cardiac cycles, such that the ultrasound image frames depict a cross-sectional view of the heart, including the ventricles and valve annuli. In particular, the ultrasound image frames may include a cross-sectional view of at least the aortic valve. Method 400 may acquire the ultrasound video by controlling an ultrasound probe, such as the ultrasound probe 236, in some examples, and so method 400 may acquire the ultrasound video in real-time. In other examples, method 400 may acquire the ultrasound video by loading ultrasound image data 226 from non-transitory memory 206. In yet other examples, method 400 may acquire the ultrasound video from a remote storage system, such as a picture archiving and communications system (PACS).

At 410, method 400 identifies frames in the ultrasound video corresponding to select cardiac phases. For example, method 400 may identify frames in the ultrasound video corresponding to systolic and diastolic phases. As illustrative and non-limiting examples, method 400 may identify frames in the ultrasound video corresponding to the ends of the systolic and diastolic phases. In one example, identifying frames corresponding to select cardiac phases comprises identifying an ROI such as the aortic valve within each ultrasound image frame of the ultrasound video, segmenting or extracting the ROI from each ultrasound image frame, and identifying the segmented or extracted ROIs that correspond to the key cardiac phases. An example method for identifying frames in ultrasound video corresponding to select cardiac phases is described further herein with regard to FIG. 5.

At 415, method 400 classifies a cardiac structure in the identified frames as a bicuspid valve or a tricuspid valve. Method 400 may classify the aortic valve as bicuspid or tricuspid, for example, by inputting each identified frame into a generative model and measuring a reconstruction error based on the output of the generative model. For example, method 400 may input extracted image frames corresponding to a first cardiac phase to a first generative model trained on images for the first cardiac phase, and method 400 may further input extracted image frames corresponding to a second cardiac phase to a second generative model trained on images for the second cardiac phase, such as the first generative model 222 and the second generative model 224 as discussed hereinabove. The generative models may be trained on images of tricuspid valves at the respective cardiac phases, such that the reconstruction error may be low when the cardiac structure depicted in the identified frames comprises a tricuspid valve but relatively high when the cardiac structure depicted in the identified frames comprises a bicuspid valve. Method 400 may thus classify the cardiac structure in each identified frame as a bicuspid valve or a tricuspid valve based on whether the reconstruction error is above or below an error threshold, respectively.

An image quality metric such as mean squared error (MSE) or the mean absolute error (MAE), as illustrative and non-limiting examples, and the error threshold may comprise a value of the image quality metric that is selected such that input images with a reconstruction error resulting in the image quality metric above the error threshold depict bicuspid images.

Further, in order to avoid false positives or false negatives, method 400 may further aggregate the number of classifications of tricuspid and bicuspid valves in the ultrasound video to classify whether the cardiac structure is a tricuspid or bicuspid valve. For example, if the ultrasound video includes a plurality of ultrasound image frames corresponding to the select cardiac phases, then method 400 may classify the cardiac structure as a bicuspid valve if the number of individual classifications of the cardiac structure as a bicuspid valve is greater than or equal to an aggregate error threshold. The aggregate error threshold may comprise a percentage of the plurality of ultrasound image frames classified as bicuspid. For example, if the plurality of ultrasound image frames corresponding to the select cardiac phases comprises ten ultrasound image frames but only one frame is classified as bicuspid, method 400 may classify the cardiac structure as tricuspid because the aggregate number of bicuspid classifications is less than an aggregate error threshold. The aggregate error threshold may be 50%, for example, or in some examples may be less than 50% or even greater than 50%. For example, the aggregate error threshold may comprise 100%, such that method 400 may classify the cardiac structure as bicuspid when all identified frames are classified as bicuspid. An example method for classifying a cardiac structure in identified frames as a bicuspid valve or a tricuspid valve is described further herein with regard to FIG. 7.

At 420, method 400 outputs a classification of the cardiac structure. For example, method 400 outputs the aggregate classification of the cardiac structure determined at 415 as a bicuspid valve or a tricuspid valve. Method 400 may output the classification to a display device 118 or 234, for example. Additionally or alternatively, method 400 may output the classification to non-transitory memory 120 or 206, for example, and/or to a PACS for reporting. Method 400 then returns.

FIG. 5 shows a high-level flow chart illustrating an example method 500 for identifying key frames in an ultrasound video including an anatomical structure at a given cardiac phase. In particular, method 500 relates to identifying frames in an ultrasound video corresponding to select cardiac phases. Method 500 may thus comprise a subroutine of method 400. Method 500 is described with regard to the system and components of FIGS. 1-3, though it should be appreciated that the method 500 may be implemented with other systems and components without departing from the scope of the present disclosure. Method 500 may be implemented as executable instructions in non-transitory memory, such as the non-transitory memory 206, that when executed by a processor, such as the processor 204, cause the processor to perform the actions described herein below. As an example, method 500 may be implemented as the key frame extraction module 210.

Method 500 begins at 505. At 505, method 500 identifies a region of interest in each frame of the ultrasound video acquired at 405. As discussed hereinabove, the region of interest in each frame may comprise the region of each ultrasound image frame depicting an aortic valve. Method 500 may therefore identify the aortic valve in each frame of the ultrasound video. Further, at 510, method 500 extracts the identified region of interest in each frame. Method 500 extracts the identified region of interest in each frame by removing the identified region of interest from each frame. Continuing at 515, method 500 registers the extracted regions of interest. For example, method 500 may temporally align the extracted regions of interest to arrest any motion, such as probe motion and/or patient motion, beyond the leaflet motion. In order to identify, extract, and align or register the regions of interest throughout the ultrasound video, the ultrasound video may be processed by a deep neural network configured to perform aortic valve localization, such as a mask R-CNN of the ROI model module 212.

Continuing at 520, method 500 identifies frames including the select cardiac phases in the registered extracted regions of interest. Method 500 may use non-negative matrix factorization to identify the select cardiac phases in the registered extracted regions of interest. For example, method 500 may model the video sequence as a linear combination of end-diastolic and end-systolic frames, and apply non-negative matrix factorization (NMF) to identify the key frames at the select cardiac phases. Method 500 may use the cardiac phase identification module 214 of the key frame extraction module 210 to identify the frames including the select cardiac phases in the registered extracted regions of interest. Once method 500 identifies the key frames, method 500 then returns.

As an illustrative example, FIG. 6 shows a set of example ultrasound images 600 illustrating an example identification of key frames including an anatomical structure at a given cardiac phase. In particular, the ultrasound images 600 include a first ultrasound image 610 with a region of interest 615 including an aortic valve at an end-systolic phase, as well as a second ultrasound image 620 with a region of interest 625 including the aortic valve at an end-diastolic phase. The regions of interest 615 and 625 may be extracted and aligned as discussed hereinabove, and the resulting extracted frames corresponding to the regions of interest 615 and 625 may be input to generative models to classify the cardiac structure depicted in the regions of interest 615 and 625 as a bicuspid valve or a tricuspid valve.

FIG. 7 shows a high-level flow chart illustrating an example method 700 for classifying an anatomical structure as a bicuspid or tricuspid valve, according to an embodiment. In particular, method 700 relates to classifying a cardiac structure depicted in identified frames of an ultrasound video corresponding to select cardiac phases as a bicuspid valve or a tricuspid valve. Method 700 may thus comprise a subroutine of method 400. Method 700 is described with regard to the system and components of FIGS. 1-3, though it should be appreciated that the method 700 may be implemented with other systems and components without departing from the scope of the present disclosure. Method 700 may be implemented as executable instructions in non-transitory memory, such as the non-transitory memory 206, that when executed by a processor, such as the processor 204, cause the processor to perform the actions described herein below. Method 700 may be implemented as the classification module 220, in some examples.

Method 700 begins at 705. At 705, method 700 inputs image frames including extracted regions of interest corresponding to select cardiac phases to respective generative models to generate images. For example, method 700 may input the extracted frames corresponding to a diastolic or end-diastolic phase to a first generative model 222, and the extracted frames corresponding to a systolic or end-systolic phase to a second generative model 224. The generative models may comprise variational autoencoders that encode each extracted frame into latent space and then decode the lower-dimensional representation of the extracted frame into image space, thereby generating an image. The generative models may be trained on images of tricuspid valves, such that resulting reconstruction errors may be relatively high if the input frames depict a bicuspid valve.

At 710, method 700 measures a reconstruction error between each generated image and the corresponding input image. The reconstruction error may comprise the difference between the generated image and the input image. Further, method 700 may calculate an error metric such as the mean squared error or the mean absolute error, as illustrative and non-limiting examples, to quantify the reconstruction error as a single value rather than a two-dimensional array of difference values.

Continuing at 715, method 700 classifies each input image with a reconstruction error greater than or equal to an error threshold as bicuspid. For example, since the generative models are trained on tricuspid images, the reconstruction error for an input image depicting a tricuspid valve may be relatively low while the reconstruction error for an input image depicting a bicuspid valve may be relatively high. Method 700 may therefore classify each input image as bicuspid when the reconstruction error, or an error metric based on the reconstruction error as discussed above, is greater than or equal to the error threshold. Further, at 720, method 700 classifies each input image with a reconstruction error less than the error threshold as tricuspid.

At 725, method 700 determines whether the number of bicuspid classifications is above a threshold. The threshold may comprise an aggregate error threshold as discussed hereinabove, which may be selected to avoid overall classifications of a tricuspid valve as bicuspid due to a small number of false positives or erroneous classifications of the tricuspid valve as bicuspid. If the number of bicuspid classifications is less than the aggregate error threshold ("NO"), method 700 continues to 735. At 735, method 700 classifies the cardiac structure as a tricuspid valve. Method 700 then returns.

However, if method 700 determines at 725 that the number of bicuspid classifications is greater than or equal to the threshold ("YES"), method 700 instead continues to 735. At 735, method 700 classifies the cardiac structure as a bicuspid valve. Method 700 then returns.

Thus, method 700 uses a generative model trained on images of tricuspid valves at a given cardiac phase to classify ultrasound image frames as depicting either a tricuspid valve or a bicuspid valve.

As illustrative examples of individual and aggregate classifications of cardiac structures in ultrasound video, FIG. 8 shows a set of images 800 illustrating generated images 820 and reconstruction errors 830 for key frames 810 in an ultrasound video resulting in classification of a tricuspid valve. The plurality of key frames 810 comprise extracted regions of interest at key cardiac phases in the ultrasound video, and includes a first image 811, a second image 812, a third image 813, a fourth image 814, a fifth image 815, and a sixth image 816. Each image frame of the plurality of key frames 810 is input to a generative model corresponding to the cardiac phase of the respective key frame, resulting in the plurality of generated images 820. The plurality of generated images 820 includes a first generated image 821 corresponding to the first image 811, a second generated image 822 corresponding to the second image 812, a third generated image 823 corresponding to the third image 813, a fourth generated image 824 corresponding to the fourth image 814, a fifth generated image 825 corresponding to the fifth image 815, and a sixth generated image 826 corresponding to the sixth image 816.

Qualitatively, the generated images 820 look visually similar to the key frames 810, as depicted. Quantitatively, the reconstruction errors 830 are measured by subtracting the generated images 820 from the respective key frames 810. The reconstruction errors 830 thus include a first error 831 for the first image 811, a second error 832 for the second image 812, a third error 833 for the third image 813, a fourth error 834 for the fourth image 814, a fifth error 835 for the fifth image 815, and a sixth error 836 for the sixth image 816. As discussed hereinabove, the anatomical structure depicted in the key frames 810 may be classified as a bicuspid valve if the reconstruction error is greater than or equal to an error threshold, and may be classified as a tricuspid valve if the reconstruction error is less than the error threshold. Error metrics such as MSE or MAE may be calculated from the reconstruction errors 830 for easier comparison to the error threshold. In the depicted example, the first error 831, the second error 832, the fourth error 834, and the fifth error 835 are below an example error threshold and therefore are classified as tricuspid. However, the third error 833 and the sixth error 836 are above the example error threshold and therefore are classified as bicuspid. However, the anatomical structure is classified as tricuspid because the number of bicuspid classifications is not above an example aggregate error threshold.

As another example, FIG. 9 shows a set of images 900 illustrating generated images 920 and reconstruction errors 930 for key frames 910 in an ultrasound video resulting in classification of a bicuspid valve. The plurality of key frames 910 comprise extracted regions of interest at key cardiac phases in the ultrasound video, and includes a first image 911, a second image 912, a third image 913, a fourth image 914, a fifth image 915, and a sixth image 916. Each image frame of the plurality of key frames 910 is input to a generative model corresponding to the cardiac phase of the respective key frame, resulting in the plurality of generated images 920. The generative models used to generate the generated images 920 comprises the same generative models used to generate the generated images 820. The plurality of generated images 920 includes a first generated image 921 for the first image 911, a second generated image 922 for the second image 912, a third generated image 923 for the third image 913, a fourth generated image 924 for the fourth image 914, a fifth generated image 925 for the fifth image 915, and a sixth generated image 926 for the sixth image 916.

Qualitatively, the generated images 920 look significantly different than the key frames 910, because the generative models are trained on images of tricuspid valves while the key frames depict a bicuspid valve. Quantitatively, the reconstruction errors 930 are measured by subtracting the generated images 920 from the respective key frames 910. The reconstruction errors 930 thus include a first error 931 for the first image 911, a second error 932 for the second image 912, a third error 933 for the third image 913, a fourth error 934 for the fourth image 914, a fifth error 935 for the fifth image 915, and a sixth error 936 for the sixth image 916. Using the same example error threshold applied to the reconstruction errors 830, each error of the reconstruction errors 930 is above the error threshold, and so each image of the key frames 910 is classified as bicuspid. Consequently, the number of bicuspid classifications is greater than or equal to the aggregate error threshold, and so the cardiac structure is classified as a bicuspid valve.

A technical effect of the present disclosure includes automatic detection of a bicuspid valve in cardiac ultrasound images. Another technical effect of the present disclosure includes the acquisition of ultrasound images. Yet another technical effect of the present disclosure includes the display of a classification of a cardiac structure as a bicuspid valve or a tricuspid valve.

In one embodiment, a method comprises acquiring ultrasound video of a heart over at least one cardiac cycle, identifying frames in the ultrasound video corresponding to at least one cardiac phase, and classifying a cardiac structure in the identified frames as a bicuspid valve or a tricuspid valve.

In a first example of the method, the method further comprises inputting the identified frames into at least one generative model to obtain generated images corresponding to the identified frames, measuring errors for the identified frames and the corresponding generated images, classifying the cardiac structure in each identified frame with an error above an error threshold as the bicuspid valve, and classifying the cardiac structure in each identified frame with an error below the error threshold as the tricuspid valve. In a second example of the method optionally including the first example, classifying the cardiac structure in the identified frames as the bicuspid valve or the tricuspid valve comprises classifying the cardiac structure in the identified frames as the bicuspid valve if the cardiac structure is classified as the bicuspid valve in a number of identified frames equal to or greater than an aggregate error threshold, and otherwise classifying the cardiac structure in the identified frames as the tricuspid valve. In a third example of the method optionally including one or more of the first and second examples, inputting the identified frames into the at least one generative model comprises inputting a first subset of the identified frames corresponding to a first cardiac phase to a first generative model, and inputting a second subset of the identified frames corresponding to a second cardiac phase to a second generative model. In a fourth example of the method optionally including one or more of the first through third examples, the first generative model is trained on ultrasound images of tricuspid valves at the first cardiac phase, and the second generative model is trained on ultrasound images of tricuspid valves at the second cardiac phase. In a fifth example of the method optionally including one or more of the first through fourth examples, the first generative model and the second generative model comprise variational autoencoders. In a sixth example of the method optionally including one or more of the first through fifth examples, identifying the frames in the ultrasound video corresponding to the at least one cardiac phase comprises extracting a region of interest in each frame of the ultrasound video to obtain a set of extracted regions of interest, modeling a sequence of the extracted regions of interest as a linear combination of a first cardiac phase and a second cardiac phase, and applying a non-negative matrix factorization to the modeled sequence to identify extracted regions of interest corresponding to the first cardiac phase and the second cardiac phase, wherein the identified frames corresponding to the at least one cardiac phase comprise the identified extracted regions of interest corresponding to the first cardiac phase and the second cardiac phase. In a seventh example of the method optionally including one or more of the first through sixth examples, the method further comprises temporally aligning the extracted regions of interest prior to modeling the sequence of the extracted regions of interest as the linear combination of the first cardiac phase and the second cardiac phase.

In another embodiment, a method comprises acquiring, with an ultrasound probe, a plurality of images of a cardiac structure at a cardiac phase, generating, with a generative model, a plurality of output images corresponding to the plurality of images, measuring an error between each output image of the plurality of output images and each corresponding image of the plurality of images, classifying the cardiac structure as abnormal if a number of images with the measured error above an error threshold is above an aggregate error threshold, and otherwise classifying the cardiac structure as normal.

In a first example of the method, the cardiac structure comprises an aortic valve, classifying the cardiac structure as abnormal comprises classifying the aortic valve as a bicuspid aortic valve, and classifying the cardiac structure as normal comprises classifying the aortic valve as a tricuspid aortic valve. In a second example of the method optionally including the first example, acquiring the plurality of images of the cardiac structure at the cardiac phase comprises acquiring a first plurality of images of the cardiac structure at a first cardiac phase and a second plurality of images at a second cardiac phase. In a third example of the method optionally including one or more of the first and second examples, generating, with the generative model, the plurality of output images corresponding to the plurality of images comprises generating, with a first generative model trained on cardiac images at the first cardiac phase, a first plurality of output images corresponding to the first plurality of images, and generating, with a second generative model trained on cardiac images at the second cardiac phase, a second plurality of output images corresponding to the second plurality of images. In a fourth example of the method optionally including one or more of the first through third examples, the first generative model and the second generative model comprise variational autoencoders configured to encode an input image into a latent space representation and decode the latent space representation into an output image.

In yet another embodiment, a system comprises an ultrasound probe and a processor configured with executable instructions in non-transitory memory that when executed cause the processor to: acquire, via the ultrasound probe, a sequence of ultrasound images of a cardiac structure over at least one cardiac cycle; identify frames in the sequence of ultrasound images corresponding to at least one cardiac phase; classify the identified frames as normal or abnormal; classify the cardiac structure as a bicuspid valve if a number of identified frames classified as abnormal is above a threshold; and otherwise classify the cardiac structure as a tricuspid valve.

In a first example of the system, the processor is further configured with executable instructions in the non-transitory memory that when executed cause the processor to input the identified frames into at least one generative model to obtain output images corresponding to the identified frames, and measure errors between the identified frames and the corresponding output images. In a second example of the system optionally including the first example, to classify the identified frames as normal or abnormal, the processor is further configured with executable instructions in the non-transitory memory that when executed cause the processor to classify each identified frame with an error above an error threshold as abnormal, and classify remaining identified frames as normal. In a third example of the system optionally including one or more of the first and second examples, the at least one generative model is trained on ultrasound images of tricuspid valves at the at least one cardiac phase. In a fourth example of the system optionally including one or more of the first through third examples, the at least one generative model comprises a variational autoencoder configured to encode an input frame into a lower-dimensional representation and decode the lower-dimensional representation into an output image. In a fifth example of the system optionally including one or more of the first through fourth examples, to identify the frames in the sequence of ultrasound images corresponding to the at least one cardiac phase, the processor is further configured with executable instructions in the non-transitory memory that when executed cause the processor to extract a region of interest in each frame of the sequence of ultrasound images to obtain a set of extracted regions of interest. In a sixth example of the system optionally including one or more of the first through fifth examples, the processor is further configured with executable instructions in the non-transitory memory that when executed cause the processor to model the set of extracted regions of interest as a linear combination of a first cardiac phase and a second cardiac phase, and apply a non-negative matrix factorization to the modeled set of extracted regions of interest to identify a first set of extracted regions of interest corresponding to the first cardiac phase and a second set of extracted regions of interest corresponding to the second cardiac phase, wherein the identified frames corresponding to the at least one cardiac phase comprise the identified extracted regions of interest corresponding to the first cardiac phase and the identified extracted regions of interest corresponding to the second cardiac phase.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
acquiring ultrasound video of a heart over at least one cardiac cycle;
identifying frames in the ultrasound video corresponding to at least one cardiac phase;

inputting the identified frames into at least one generative model to obtain generated images corresponding to the identified frames;
measuring errors for the identified frames and the corresponding generated images;
classifying a cardiac structure in the identified frames with an error above an error threshold as a bicuspid valve and;
classifying the cardiac structure in each identified frame with an error below the error threshold as a tricuspid valve.

2. The method of claim 1, wherein classifying the cardiac structure in the identified frames as the bicuspid valve or the tricuspid valve comprises:
classifying the cardiac structure in the identified frames as the bicuspid valve if the cardiac structure is classified as the bicuspid valve in a number of identified frames equal to or greater than an aggregate error threshold; and
otherwise classifying the cardiac structure in the identified frames as the tricuspid valve.

3. The method of claim 1, wherein inputting the identified frames into the at least one generative model comprises:
inputting a first subset of the identified frames corresponding to a first cardiac phase to a first generative model; and
inputting a second subset of the identified frames corresponding to a second cardiac phase to a second generative model.

4. The method of claim 3, wherein the first generative model is trained on ultrasound images of tricuspid valves at the first cardiac phase, and wherein the second generative model is trained on ultrasound images of tricuspid valves at the second cardiac phase.

5. The method of claim 3, wherein the first generative model and the second generative model comprise variational autoencoders.

6. The method of claim 1, wherein identifying the frames in the ultrasound video corresponding to the at least one cardiac phase comprises:
extracting a region of interest in each frame of the ultrasound video to obtain a set of extracted regions of interest;
modeling a sequence of the extracted regions of interest as a linear combination of a first cardiac phase and a second cardiac phase; and
applying a non-negative matrix factorization to the modeled sequence to identify extracted regions of interest corresponding to the first cardiac phase and the second cardiac phase, wherein the identified frames corresponding to the at least one cardiac phase comprise the identified extracted regions of interest corresponding to the first cardiac phase and the second cardiac phase.

7. The method of claim 6, further comprising temporally aligning the extracted regions of interest prior to modeling the sequence of the extracted regions of interest as the linear combination of the first cardiac phase and the second cardiac phase.

8. A method, comprising:
acquiring, with an ultrasound probe, a plurality of images of a cardiac structure at a cardiac phase;
generating, with a generative model, a plurality of output images corresponding to the plurality of images;
measuring an error between each output image of the plurality of output images and each corresponding image of the plurality of images;
classifying the cardiac structure as abnormal if a number of images with the measured error above an error threshold is above an aggregate error threshold; and
otherwise classifying the cardiac structure as normal.

9. The method of claim 8, wherein the cardiac structure comprises an aortic valve, wherein classifying the cardiac structure as abnormal comprises classifying the aortic valve as a bicuspid aortic valve, and wherein classifying the cardiac structure as normal comprises classifying the aortic valve as a tricuspid aortic valve.

10. The method of claim 8, wherein acquiring the plurality of images of the cardiac structure at the cardiac phase comprises acquiring a first plurality of images of the cardiac structure at a first cardiac phase and a second plurality of images at a second cardiac phase.

11. The method of claim 10, wherein generating, with the generative model, the plurality of output images corresponding to the plurality of images comprises:
generating, with a first generative model trained on cardiac images at the first cardiac phase, a first plurality of output images corresponding to the first plurality of images; and
generating, with a second generative model trained on cardiac images at the second cardiac phase, a second plurality of output images corresponding to the second plurality of images.

12. The method of claim 11, wherein the first generative model and the second generative model comprise variational autoencoders configured to encode an input image into a latent space representation and decode the latent space representation into an output image.

13. A system, comprising:
an ultrasound probe; and
a processor configured with executable instructions in non-transitory memory that when executed cause the processor to:
acquire, via the ultrasound probe, a sequence of ultrasound images of a cardiac structure over at least one cardiac cycle;
identify frames in the sequence of ultrasound images corresponding to at least one cardiac phase;
classify the identified frames as normal or abnormal;
classify the cardiac structure as a bicuspid valve if a number of identified frames classified as abnormal is above a threshold; and
otherwise classify the cardiac structure as a tricuspid valve.

14. The system of claim 13, wherein the processor is further configured with executable instructions in the non-transitory memory that when executed cause the processor to:
input the identified frames into at least one generative model to obtain output images corresponding to the identified frames; and
measure errors between the identified frames and the corresponding output images.

15. The system of claim 14, wherein, to classify the identified frames as normal or abnormal, the processor is further configured with executable instructions in the non-transitory memory that when executed cause the processor to:
classify each identified frame with an error above an error threshold as abnormal; and
classify remaining identified frames as normal.

16. The system of claim 14, wherein the at least one generative model is trained on ultrasound images of tricuspid valves at the at least one cardiac phase.

17. The system of claim 14, wherein the at least one generative model comprises a variational autoencoder configured to encode an input frame into a lower-dimensional representation and decode the lower-dimensional representation into an output image.

18. The system of claim 13, wherein, to identify the frames in the sequence of ultrasound images corresponding to the at least one cardiac phase, the processor is further configured with executable instructions in the non-transitory memory that when executed cause the processor to:
   extract a region of interest in each frame of the sequence of ultrasound images to obtain a set of extracted regions of interest.

19. The system of claim 18, wherein the processor is further configured with executable instructions in the non-transitory memory that when executed cause the processor to:
   model the set of extracted regions of interest as a linear combination of a first cardiac phase and a second cardiac phase; and
   apply a non-negative matrix factorization to the modeled set of extracted regions of interest to identify a first set of extracted regions of interest corresponding to the first cardiac phase and a second set of extracted regions of interest corresponding to the second cardiac phase, wherein the identified frames corresponding to the at least one cardiac phase comprise the identified extracted regions of interest corresponding to the first cardiac phase and the identified extracted regions of interest corresponding to the second cardiac phase.

* * * * *